（12） United States Patent
Wilser et al.

(10) Patent No.: US 7,678,056 B2
(45) Date of Patent: Mar. 16, 2010

(54) ARRAY ROTATION FOR ULTRASOUND CATHETERS

(75) Inventors: Walter T. Wilser, Cupertino, CA (US); Lex J. Garbini, San Gregorio, CA (US); Jian Hua Mo, Milpitas, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 335 days.

(21) Appl. No.: 11/904,776

(22) Filed: Sep. 27, 2007

(65) Prior Publication Data

US 2008/0027327 A1    Jan. 31, 2008

Related U.S. Application Data

(62) Division of application No. 11/012,389, filed on Dec. 14, 2004.

(51) Int. Cl.
*A61B 8/14* (2006.01)
(52) U.S. Cl. .................. 600/463; 600/437; 600/439; 600/459; 600/462; 600/466
(58) Field of Classification Search ............... 600/407, 600/408, 437–463; 601/2–4
See application file for complete search history.

(56) References Cited

U.S. PATENT DOCUMENTS 4,951,677 A    8/1990    Crowley et al.
5,150,715 A    9/1992    Ishiguro et al.
5,353,354 A    10/1994   Keller et al.
5,375,602 A    12/1994   Lancee et al.
5,413,107 A    5/1995    Oakley et al.
5,529,070 A    6/1996    Augustine et al.
5,671,748 A    9/1997    Itoi
5,840,031 A    11/1998   Crowley
5,932,035 A    8/1999    Koger
5,951,494 A    9/1999    Wang et al.
6,165,127 A    12/2000   Crowley
6,793,635 B2   9/2004    Ryan et al.
6,796,945 B2   9/2004    Belef et al.
6,814,727 B2   11/2004   Mansouri-Ruiz
7,037,271 B2   5/2006    Crowley

*Primary Examiner*—Long V Le
*Assistant Examiner*—Sanjay Cattungal

(57) ABSTRACT

A transducer array is connected with a catheter housing. As the transducer array is rotated, the catheter housing also rotates. As a result, at least a portion of the catheter housing twists about a longitudinal axis. By applying rotation in a controlled way, such as with a motor, a plurality of two-dimensional images for three-dimensional reconstruction may be obtained. The rotation of the catheter housing may limit the total amount of rotation of the array, such as rotating the array through a 90 degree or less amount of rotation about the longitudinal axis. The housing of the catheter is formed with a soft section. The softer material allows for a greater amount or increased ease for twisting the catheter.

11 Claims, 1 Drawing Sheet

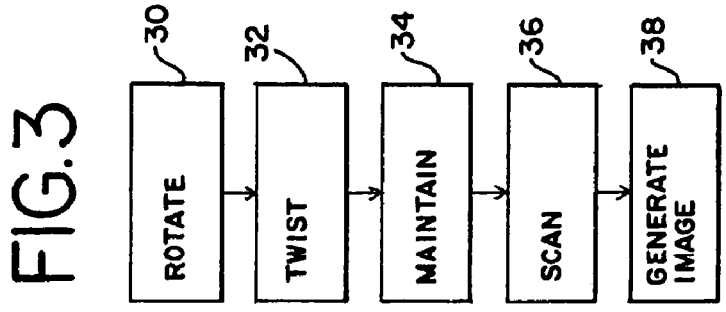
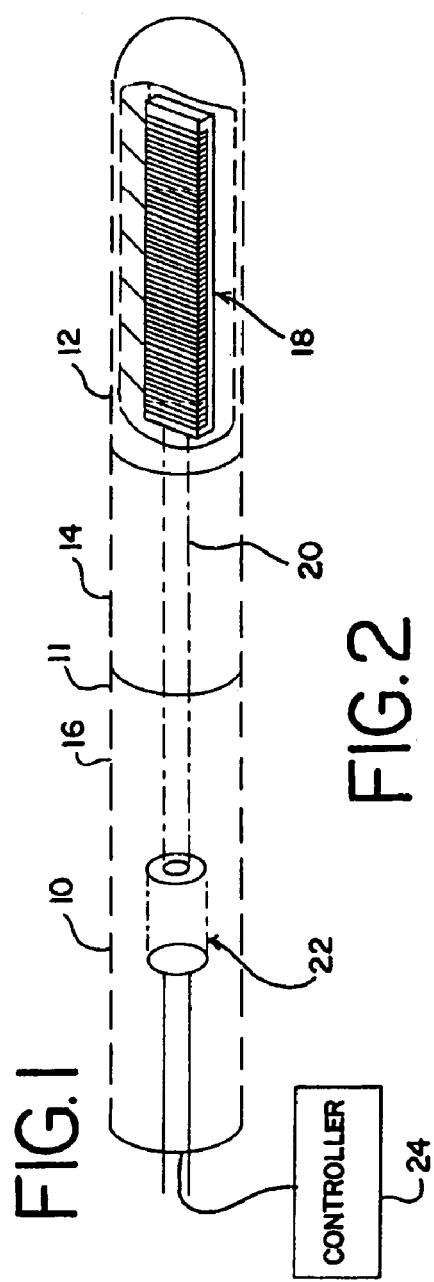
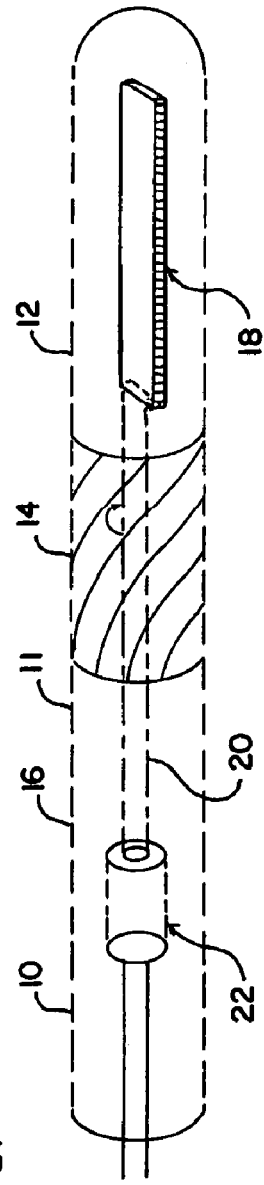
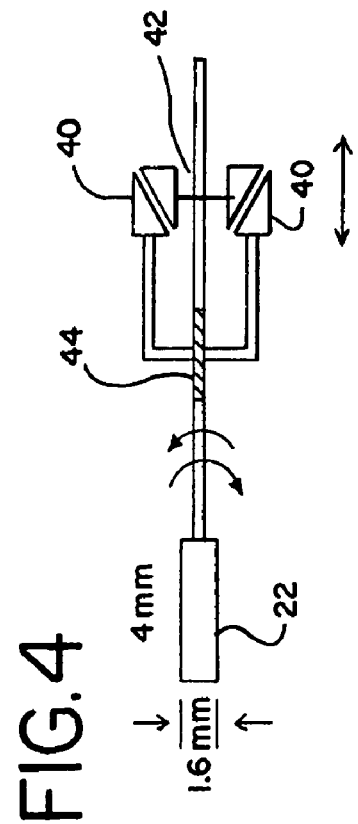

ary rotation for ultrasound catheters

CROSS-REFERENCE TO RELATED APPLICATION

This application is a divisional of U.S. patent application No. 11/012,389, filed Dec. 14, 2004.

BACKGROUND

The present invention relates to ultrasound imaging with catheters. In particular, two- or three-dimensional imaging is provided with an array in a catheter.

In the AcuNav™ catheter, a 64 element array of elements extends along a longitudinal axis of the catheter. The array is positioned at a tip portion for scanning a two-dimensional region or plane along the longitudinal axis. Other catheters have been proposed where one or more elements are rotated within the catheter about the longitudinal axis to scan in a plane perpendicular to the axis.

During use, a catheter is inserted within the circulatory system of the patient. The flexibility along the catheter may vary as a function of position, such as having a more flexible tip portion for off-axis bending while guiding the catheter. The catheter is guided through the circulatory system to position the ultrasound transducer adjacent to a desired location. Guide wires or rotation of the entire catheter are used to position the image plane at the desired location. Various stresses and strains may cause bending and slight twisting along the catheter. Images are then generated of the desired location.

By only scanning along a two-dimensional plane, identifying the desired location may be more difficult. Three-dimensional imaging has been proposed for more easily identifying a region of interest. Since catheters are small, such as having a 3 mm diameter, it may be difficult to position a two-dimensional array within the catheter. Three-dimensional imaging may be provided by moving the imaging plane of the one-dimensional array. For example, the catheter is slowly inserted further or withdrawn from a current position to create a plurality of cross sectional scans using a rotating array. However, the imaging plane position for accurate or higher resolution three-dimensional reconstruction may be difficult.

BRIEF SUMMARY

By way of introduction, the preferred embodiments described below include systems, methods and catheters for ultrasound imaging of a volume. Rotational forces are applied to a transducer array. The transducer array is connected with the catheter housing. As the transducer array rotates, the catheter housing also rotates. As a result, at least a portion of the catheter housing twists about a longitudinal axis. By applying rotation in a controlled way, such as with a motor, a plurality of two-dimensional images for three-dimensional reconstruction may be obtained. The rotation of the catheter housing may limit the total amount of rotation of the array, such as rotating the array through a 90 degree or less amount of rotation about the longitudinal axis. In one embodiment, the housing of the catheter is formed with a flexible or softer section. The softer material allows for a greater amount of or increased ease for twisting the catheter.

In a first aspect, a catheter is provided for ultrasound imaging of a volume. A transducer section of the catheter houses an ultrasound transducer array. The array is connected with the transducer section. A motor is spaced from the transducer section. A drive shaft connects the motor with the transducer section. A flexible section of the catheter connects with the transducer section. The drive shaft extends through at least a portion of the flexible section. The drive shaft is operable to rotate the ultrasound transducer array and connected transducer section substantially about a longitudinal axis of the catheter in response to force from the motor. The flexible section is operable to twist about the longitudinal axis in response to the rotation of the transducer section.

In a second aspect, a system is provided for ultrasound imaging of a volume. A catheter has a housing. An ultrasound transducer array of elements is within the housing. A shaft is also within the housing. The shaft connects with the ultrasound transducer array of elements. The ultrasound transducer array is operable to rotate about a longitudinal axis of the housing in response to rotation of the shaft. The housing is operable to twist from a first portion to a second portion of the housing. An amount of twist corresponds to an amount of rotation of the ultrasound transducer array.

In a third aspect, a method is provided for scanning a volume with an ultrasound catheter. A transducer array is rotated about a longitudinal axis of the ultrasound catheter. A first portion of a housing of the ultrasound catheter is also rotated about the longitudinal axis with the transducer array. The transducer array and first portion rotate a substantially same amount. A second portion of a housing twists about the longitudinal axis in response to the rotation of the transducer array, the first portion of the housing or both the transducer array and the first portion. A third portion of the housing of the catheter is maintained substantially free of the twisting and rotation of the second and first portions during the twisting and rotation of the second and first portions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a side view of one embodiment of a catheter for ultrasound imaging;

FIG. 2 is a side view of the catheter of FIG. 1 in a twisted position;

FIG. 3 is a flow chart of one embodiment of a method for ultrasound imaging with a catheter; and FIG. 4 is a cross-section view of one embodiment of a motor for rotating a transducer.

DETAILED DESCRIPTION OF THE DRAWINGS AND PRESENTLY PREFERRED EMBODIMENTS

An ultrasound transducer stack within a catheter is rotated about the longitudinal axis of the catheter for positioning a two-dimensional plane at a desired location or generating a three-dimensional image. A micro-motor or other source of force rotates the transducer stack. While a rotating joint may be used, seals and cable routing of a rotating joint are difficult to implement in a small space of a typical catheter. To avoid or limit these difficulties, the catheter housing is radially deflected to allow rotation of the transducer array. For example, a housing of low durometer or soft Pebax is provided with a rigid shaft. The rigid shaft transmits force for rotation of the array. The soft housing allows twisting of the catheter about the longitudinal axis.

FIG. 1 shows a system for ultrasound imaging a region or volume from within a patient. The system includes a catheter 10 and a controller 24. The controller 24 is positioned outside of, away from or within the catheter 10. In one embodiment, the controller 24 is positioned within an ultrasound imaging system connected with the catheter 10.

The catheter 10 is adapted for insertion within a circulatory or venous system. For example, the catheter 10 is about 5 mm or less in diameter. Larger or smaller catheters may be used. The catheter 10 includes a sterile or other safe coating for use within a patient. One or more guide wires or other structures for steering the catheter 10 may be provided. In other embodiments, the catheter 10 is adapted for insertion through a portal or tube within another structure, such as a guide catheter. Any now known or later developed catheter structures may be used, such as providing an elongated flexible tip with a narrower diameter than the main body of the catheter 10.

The catheter 10 includes a housing 11, a transducer array 18, a shaft 20 and a motor 22. Additional, different or fewer components may be provided, such as providing the motor 22 external to the housing 11 in a handle. As another example, guide wires, ports, tubes, circuitry, signal cabling, or other now known or later developed catheter structure is provided.

The housing 11 includes one or more sections 12, 14, 16. For example, a transducer section 12 connects to a motor section 16 through a flexible section 14. The transducer section 12 corresponds to a section of the catheter 10 surrounding or associated with the transducer array 18. Similarly, the motor section 16 corresponds to a portion of the housing 11 associated with the motor 22. The transducer and motor sections 12, 16 may be of any length, such as less than, the same as or greater than the length of the respective transducer array 18 and motor 22. The sections 12, 14, 16 are provided at a tip of the catheter 10, such as a region 1-10 inches in length at a distal portion of the catheter 10 from a handle. In other embodiments, all, one or more of the sections has a greater or lesser length. The flexible section 14 extends over any distance, such as a centimeter, an inch, inches, or the entire extent of the housing 11 away from the transducer 18.

In one embodiment, the housing 11 is the same for each of the different sections 12, 14, 16. For example, each of the sections 12, 14, 16 are formed from a same extruded material, such as a polymer. Other now known or later developed materials may be used. In other embodiments, the housing 11 of the catheter 10 varies as a function of the section 12, 14, 16. In one embodiment, 35 to 25 shore D Pebax, Nylon or Silicone is used. In other embodiments, the housing 11 of the catheter 10 varies as a function of the section 12, 14, 16. For example, the extrusion process is varied or the material used for the extrusion is varied as a function of the sections 12, 14, 16. The flexible section 14 is formed from a softer material or the same material processed to be softer than the harder transducer section 12 and/or motor section 16. While represented as sharp distinctions between the sections 12, 14, 16 by the circumferential lines in FIG. 1, the difference in hardness may gradually vary between the sections 12, 14, 16. The softer flexible section 14 provides a lower durometer portion of the housing 11. In alternative embodiments, the flexible section 14 extends over the motor 22, over all or a portion of the transducer 18 or is separate from both. The motor section 16 and/or the transducer section 12 may have a same softness or hardness as the flexible section 14, as each other or be different.

The flexible section 14 is operable to twist about the longitudinal axis of the catheter 10 in response to rotation of the transducer section 12 and the transducer 18. FIG. 2 shows the flexible section 14 twisting as compared to the motor section 16 and the transducer section 12. The transducer 18 and transducer section 12 are shown rotated by about 45 degrees. Twist lines are shown in the flexible section 14 associated with the 45 degrees of twisting. The twisting is shown just by the flexible section 14, but may extend into or through the motor section 16 and/or transducer section 12. Where the flexible section 14 is softer or more flexible than other sections 12, 16, a greater amount of twisting may be provided in the flexible section 14 than the other sections. The twisting may occur from a point of first contact of the transducer 18 with the transducer section 12 through to a point of contact or connection of the motor 22 to the motor section 16 of the housing 11. Where the sections have similar flexibility, the amount of twisting in any one section 12, 14, 16 is based on the length of the section.

The amount of the twist corresponds to the amount of rotation of the ultrasound transducer array. For example, where the ultrasound transducer array is rotated about the longitudinal axis by 8 degrees, 15 degrees, 30 degrees, 45 degrees, 90 degrees, 180 degrees, 270 degrees or other amount, the twist absorbs or is rotated the same amount from the transducer 18 and the portion of the transducer section 12 through to the motor 22 and a portion of the motor section 16. Where the motor 22 or the transducer 18 mounts to the housing spaced away from the motor 22 or the transducer 18, the mounting location determines the range of twist. The amount of twist is about the same since the motor 22 and the transducer 18 connect with the housing 11.

The catheter 10 and associated housing 11 allow for angular repositioning of the transducer array 18 about the longitudinal axis by absorbing the rotation through twisting in the catheter 10. The amount of twisting is more than incidental. The motor 22 and shaft 20 communicate intentional rotation to the transducer array 18 for rotation about the longitudinal axis. The twisting is in addition to or other than twisting provided by rotating the catheter 10 on the handle externally to the patient while the catheter 10 is within the patient.

The ultrasound transducer 18 is a one-dimensional array of piezoelectric, membrane or other now known or later developed acoustic transducers. Multidimensional, such as 1.25, 1.5, 1.75 or two-dimensional arrays may be used. The transducer array 18 includes a plurality of elements extending along the longitudinal axis of the catheter 10. The elements may be spaced from the axis or centered on the axis. As the transducer array 18 rotates about the longitudinal axis, the face of the transducer associated with the elements rotates. The imaging plane associated with the transducer elements also rotates. A mechanical elevation focus is provided in one embodiment, but an acoustical window without mechanical focusing may be provided in other embodiments.

The transducer array 18 connects with the transducer section 12 of the housing 11. For example, the transducer array 18 and its associated stack, such as backing and matching layers, are pressure fitted within the transducer section 12. Alternatively, bonding, riveting, bolts, clips or other attachment mechanisms substantially fixedly attach the transducer array 18 to the housing 11. As the ultrasound transducer array 18 or the transducer section 12 rotates, the connection provides for the other of the transducer section 12 or the transducer array 18 to also rotate. For example, force supplied by the motor 22 along the shaft 20 applies direct rotational force to the transducer array 18, the transducer section 12 or both for rotating both. The connection between the transducer section 12 and the transducer array 18 may be direct or indirect, such as connecting a backing block or other support structure of the transducer array 18 directly to or through one or more other components to the housing 11. The connection may allow some relative rotation or slippage of the transducer array 18 separate from or differently from the transducer section 12. For example, the ultrasound transducer array 18 is operable to rotate a few degrees within the housing 11 before also forcing the housing 11 at the transducer section 12 to rotate along the longitudinal axis.

The motor 22 is a micro motor, such as a servo, piezo, stepper, micro-brushless DC, or other motor. In one embodiment, the motor 22 is sufficiently small, such as being 3 mm or less in diameter, for being positioned within the catheter 10. A gear box, such as a planetary gear head having a 50 to 1 or other gearing reduction, is provided as part of the motor 22 or separate from the motor 22. The motor 22 is operable to cause rotation of the shaft 20. In one embodiment, the shaft 20 and the motor 22 are positioned in a central position along the longitudinal axis of the catheter 10, but may be offset from the longitudinal axis. The motor 22 and associated gearing allow the application of sufficient torque along the shaft 20 to rotate the transducer array 18 and cause twisting of the housing 11. The motor 22 is spaced from the ultrasound transducer array 18 by the shaft 20. In one embodiment, the total force or torque applied by the motor 22 is matched to the resistance caused by the twisting of the housing 11 such that the housing 11 limits the total rotation of the transducer array 18. For example, the limitation may be 360 degrees or less, such as 90 degrees, 20 degrees, 10 degrees or other limitation on rotation in a given direction from a neutral position. In alternative embodiments, the motor 22 supplies sufficient torque but is limited by control of the motor 22 to avoid undesired wrapping of internal components about the shaft 20. Rotation beyond 360 degrees may be provided.

FIG. 4 shows another embodiment of the motor 22. The motor 22 is connected to a rotational speed reducing mechanism. Reduction in rotational speed may be useful for low torque or inaccurate angular positioning motors 22. Part 44 of the shaft 42 is threaded to translate rotation into lateral motion of the wedges 40. The lateral motion is translated back into rotation by the matched wedges 40. As the wedges 40 connected with the threading move laterally, rotation about the same axis as the shaft 42 is induced in the matched wedges 40. With fine threads on the first part 44 and rotationally matched wedges 40, the rotation is reduced several fold, but any amount of reduction may be provided. Alternatively, a reduction gear box is used. In yet other alternative embodiments, gearing, cams or other mechanisms convert rotation in one direction into a wobble or back and forth rotation.

Another embodiment uses a push-pull motor or solenoid. The lateral motion of the motor 22 is translated into rotation by matched wedges, gearing, rotational connection or other mechanisms.

The shaft 20 is a drive shaft for transmitting torque from the motor 22 to the ultrasound transducer array 18. The shaft 20 is metal, plastic, polymer, fiberglass, resin or other now known or later developed rigid or semi-rigid material. The shaft 20 extends through the housing 11, including the flexible section 14. The shaft 20 is more rigid than the flexible section 14 of the housing 11 so that the torque may be transmitted for rotating the transducer array 18 while the flexible section 14 twists. The shaft connects with the motor 22 directly, such as being part of the motor, or indirectly through gearing. The shaft 20 connects directly or indirectly to the transducer array 18, the transducer section 12 or both.

The shaft 20 is operable to rotate the transducer array and the connected transducer section 12 substantially about the longitudinal axis of the catheter 10 in response to force from the motor 22. Using control of the motor 22 or torsional limitations to the twisting of the housing 11, the ultrasound transducer array 18 is operable to rotate less than 360 degrees in one embodiment, but greater or lesser limitations on rotations are provided in other embodiments. The shaft 20 is free of direct connection to the housing 11 other than for connection with the transducer array 18 or in the flexible section 14. The housing 11 may apply friction to the shaft 20 or may be spaced away from the shaft 20 using one or more bearings for allowing rotation.

The controller 24 is a processor, digital signal processor, application specific integrated circuit, field programmable gate array, digital circuit, analog circuit or combinations thereof. The controller 24 is operable to control operation of the motor 22, but may also be used for controlling other operations, such as transmit or receive operations for the transducer array 18. The control wires from the controller 24 extend through the housing 11 for connection with the motor 22. Separate cabling may be provided for the transducer array 18 for transmit and receive operation. Since the rotation of the transducer array 18 is limited, the cabling for transmit and receive operations may connect directly with the flexible circuit or the transducer array 18. In one embodiment, the controller 24 is a mechanical torsional resonant circuit. The controller 24 is operable to cause the motor 22, shaft 20 and ultrasound transducer array 18 to rotate or oscillate about the longitudinal axis over an arch. In one embodiment, the rotation is over a 270 degree range or less, but greater rotation may be provided. In one embodiment, the shaft 20 is oscillated to rotate the transducer array about an arc of 20 degrees or less, such as 10 or fewer degrees to each side of neutral. The housing 11 twists along the flexible section 14 in opposite direction sequentially in response to the oscillation. In alternative embodiments, the controller 24 causes movement or repositioning of the transducer array 18 without oscillation.

FIG. 3 shows one embodiment of a method for scanning a volume with an ultrasound catheter. The method uses the catheter 10 and associated system shown in FIGS. 1 and 2 or a different catheter. Additional, different or fewer acts may be provided, such as providing acts 30 and 32 without acts 34, 36, and/or 38.

In act 30, the transducer array and a portion of the housing of the ultrasound catheter are rotated about the longitudinal axis of the catheter. Both the portion of the housing and the transducer array rotate substantially a same amount. Some difference in rotation may result from a slippage between the transducer array and the transducer section 12. A shaft within the housing rotates. The shaft is connected directly or indirectly with the portion of the housing, the transducer array or both the portion of the housing and the transducer array to supply torque. In response to a motor driving the shaft, torque is applied to the transducer array. The rotational motion is over any range of freedom, such as being less than 360 degrees. For example, the transducer array is only rotated within an arc about the longitudinal axis of 30 or fewer degrees. Other lesser or greater amounts of rotation may be provided.

In act 32, another portion of the housing is twisted about the longitudinal axis in response to rotation of the transducer array, the portion of the housing connected to the transducer array or both. As a result of the twisting, a more distal portion of the housing rotates further than a more proximal portion of the housing. For example, a portion of soft or softer material than other portions of the housing 11 twists to a greater extent closer to the transducer than a portion further away from the transducer. The soft portion of the housing absorbs at least some of or all of the rotation by twisting. The amount of twisting corresponds to the amount of rotation, such as being the same. In one embodiment, the greatest extent of twisting is 15 degrees in one direction. Twisting is provided in an opposite direction for a greatest extent of 15 degrees, providing at a 30 degrees of arc. The housing is free of twisting or neutral at zero degrees. Asymmetrical amounts of twisting may be provided in alternative embodiments.

The twisting is associated with oscillation in one embodiment. An ultrasound transducer is oscillated about a particular angular position, such as an angular position associated with the neutral position of the housing 11. In response to the oscillation of the ultrasound transducer, twisting is performed in opposite directions. The twisting is provided along a straight or bent portion of the catheter. For example, the catheter curves to conform to a path of a vessel. The twisting is performed along the longitudinal axis as it curves through the vessel.

In act 34, a portion of the housing of the catheter is maintained substantially free of twisting during the rotation and twisting of other portions of the housing. For example, a portion of the housing adjacent to the motor is maintained relatively free of twisting where the flexible section between the motor and the transducer array absorbs the twisting caused by the rotation of the transducer array. In one embodiment, the motor is positioned within the catheter spaced away from a handle so that the twisting is mostly transmitted along a portion of a catheter spaced away from the handle. Alternatively, twisting is transmitted along a majority of the catheter, such as to a portion external to the patient. Where the motor is positioned in a tip portion, the twisting is substantially, entirely or mostly isolated to the tip portion.

In act 36, the ultrasound transducer is used to scan along a plurality of planes. Using electronic or mechanical steering, acoustic energy is sequentially transmitted along a plurality of scan lines within a plane. Since different scan lines are transmitted at different times, the plane scanned is a general plane that may allow for some movement of the transducer array during the planar scan. A plurality of planes is scanned at different positions of rotation about the longitudinal axis. Using controlled movement of the motor or sensing a position of the transducer array, the relative locations of data associated with the different planes is obtained. As the transducer array moves or rotates, additional data is obtained.

In act 38, an image representing a volume is generated as a function of data acquired along the plurality of planes. Using the relative position of the scan lines or planes, data is interpolated or otherwise used to generate a three-dimensional representation. For example, data is interpolated to a three-dimensional Cartesian grid and then volume rendering is performed. In alternative embodiments, one or more two-dimensional images associated with a same or different plane are generated. For example, the catheter is positioned adjacent to tissue to be ablated. The transducer array is then rotated until the desired tissue is identified. Once identified, the position of the ultrasound transducer relative to the desired tissue is maintained by ceasing rotation or continuing rotation to counteract any movement of the catheter.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for scanning a volume with an ultrasound catheter, the method comprising:
    (a) providing an ultrasound catheter having a housing, the housing comprising a first portion having a transducer array, a third portion having a motor, and a second flexible portion between the first and third portions;
    (b) rotating a transducer array about a longitudinal axis of the ultrasound catheter;
    (c) rotating the first portion of the housing of the ultrasound catheter about the longitudinal axis with the transducer array a substantially same amount;
    (d) twisting the second portion of the housing about the longitudinal axis in response to the rotation of the transducer array, the first portion or combinations thereof;
    (e) maintaining the third portion of the housing substantially free of the twisting and rotation of the second and first portions during the twisting and rotation of the second and first portions;
    (f) scanning with the ultrasound transducer along a plurality of planes rotated about the longitudinal axis in response to (b) and (c); and
    (g) generating an image representing the volume as a function of data along the plurality of planes.

2. The method of claim 1 wherein (b) and (c) comprise rotating a shaft within the housing, the shaft connected with the first portion, the transducer array or both the first portion and the transducer array.

3. The method of claim 1 wherein (b) and (c) comprise rotation in response to a motor in the third portion.

4. The method of claim 1 wherein (e) comprises maintaining the third portion, the third portion being spaced away from a handle and adjacent to a tip portion.

5. The method of claim 1 wherein (d) comprises providing the second portion as softer than the third portion.

6. The method of claim 1 wherein (d) comprises rotating a distal portion of the second portion to a greater extent than a proximal portion of the second portion about the longitudinal axis.

7. The method of claim 1 wherein (b) and (c) comprise always rotating less than 360 degrees.

8. The method of claim 1 wherein (b) and (c) comprise rotating only within an arc about the longitudinal axis of 30 degrees.

9. The method of claim 8 wherein (d) comprises twisting a first direction less than 15 degrees at a greatest extent of twisting and twisting in an opposite, second direction less than 15 degrees at the greatest extent of twisting, the housing free of twisting at 0 degrees.

10. The method of claim 7 further comprising:
    oscillating the ultrasound transducer;
    wherein (d) comprises twisting in opposite directions in response to the oscillation of the ultrasound transducer.

11. The method of claim 1 further comprising:
    converting rotational motion at a first speed of a motor to lateral motion and the later motion to rotational motion at a second speed different than the first speed, the rotational motion at the second speed operable to rotation the transducer array.

* * * * *